United States Patent [19]

Höltke et al.

[11] Patent Number: 5,354,657

[45] Date of Patent: Oct. 11, 1994

[54] PROCESS FOR THE HIGHLY SPECIFIC DETECTION OF NUCLEIC ACIDS IN SOLID

[76] Inventors: Hans J. Höltke, Kirchenstrasse 1, D-8132 Tutzing; Rudolf Seibl, Saalangerstrasse 46, D-8122 Penzberg; Christoph Kessler, Fraunhofer Strasse 12, D-8000 München 5; Ralf Mattes, Friedrich-Zundel-Strasse 14, D-7000 Stuttgart 75; Hermann Graf, Johannes-Tanner-Strasse 2a, D-8000 München 60, all of Fed. Rep. of Germany

[21] Appl. No.: 993,820

[22] Filed: Dec. 18, 1992

Related U.S. Application Data

[63] Continuation of Ser. No. 919,506, Jul. 24, 1992, abandoned, which is a continuation of Ser. No. 709,071, May 30, 1991, abandoned, which is a continuation of Ser. No. 296,444, Jan. 12, 1989, abandoned.

[30] Foreign Application Priority Data

Jan. 12, 1988 [DE] Fed. Rep. of Germany ....... 3800644

[51] Int. Cl.$^5$ .................. C12Q 1/68; C07H 21/04; C12N 15/00
[52] U.S. Cl. ...................... 435/6; 536/24.3; 935/77; 935/78
[58] Field of Search ............ 435/6; 536/24.3; 935/77, 78

[56] References Cited

U.S. PATENT DOCUMENTS

| | | | |
|---|---|---|---|
| 4,358,535 | 11/1982 | Falkaw et al. | 435/6 |
| 4,486,539 | 12/1984 | Ranki et al. | 435/504 |
| 4,581,333 | 4/1986 | Kourilski et al. | 435/6 |

FOREIGN PATENT DOCUMENTS

| | | | |
|---|---|---|---|
| 63879 | 11/1982 | European Pat. Off. | |
| 0192168 | 8/1986 | European Pat. Off. | 435/6 |
| 198662 | 10/1986 | European Pat. Off. | |
| 3431536 | 3/1986 | Fed. Rep. of Germany | 435/6 |
| 8607387 | 12/1986 | PCT Int'l Appl. | 435/6 |
| 8802785 | 4/1988 | World Int. Prop. O. | |

OTHER PUBLICATIONS

Schäfer Nucleic Acids Res. 16(19):9344 (1988).
BMBiochemica 5(4) Jul. 1988 pp. 1, 4 & 5 (issued by Boehringer Mannheim Biochemicals).
Rigby et al. J. Mol. Biol. (1977) 113:237.
Feinberg et al. Analytical Biochem 132:6–13 (1983).
Hart et al. Organic Chemistry; Haughton Mifflin Co. N.Y. N.Y. (1972) p. 473.
Boehringer Mannheim Biochemicals Catalog 1989 p. 465.
DIG System–Literature (Dec. 1990) Molecular Biology.

(List continued on next page.)

Primary Examiner—Mindy B. Fleisher

[57] ABSTRACT

The present invention provides a process for the detection of nucleic acids of definite sequence by hybridisation with two single-stranded nucleic acid probes present in the same solution phase complementary to different regions of the nucleic acid to be detected, one nucleic acid probe serving as detector probe and containing as labelling at least one hapten bound via a chemical linkage and the other nucleic acid probe serving as capturing probe and being bound to a solid matrix, wherein, as hapten, a steroid is used which on at least one position of the detector probe, which does not participate in the hydrogen bridge formation with the nucleic acid to be detected, is covalently bound via a bridge of at least four atoms, the nucleic acid to be detected, present in solution, is incubated with the detector probe and the capturing probe in any desired sequence, whereby the binding of the capturing probe on the matrix with the nucleic acid to be detected is brought about before, during or after the incubation, the remaining solution is separated off from the matrix-bound complex of the capturing probe, nucleic acid to be detected and detector probe and the complex detected via an anti-hapten antibody which is labelled.

22 Claims, 10 Drawing Sheets

OTHER PUBLICATIONS

Azzi, A. et al. (1990) Journal of Virol. Methods 27:125–134.

Baldino, F., Jr. Meth. In Neurosciences 1989 Acad. Press pp. 282–292.

Brunet, B., et al. (1989) Eur. J. Clin. Microbiol. Infect. Dis. vol. 8, pp. 636–638.

Casacuberta, J. M., et al. (1988) Nucleic Acids Res. vol. 16, No. 24. p. 39.

S. Dooley, et al. (1988) Nucleic Acids Research vol. 16, No. 24, p. 40.

Technical Tips, TIG Nov. 1989, vol. 5, No. 11.

Furuta, Y., et al. J. Clin. Pathology 43:806–809, 1990.

Gallego, L., et al. (1990) Jour. Microbiol. Methods II, pp. 261–267.

Gentilomi, G., et al. (1989) Jour. Immunological Methods, 125:177–183.

Heiles, H. F. J., et al. (1988) Biotechniques, vol. 6, No. 10. 978–981.

Heino, P., et al. (1989) Jour. Virological Methods 26:331–338.

Herrington, C. S., et al. (1989) J. Clin. Pathol. 42:592–600.

Herrington, C. S., et al. (1989) J. Clin. Pathol. 42:601–606.

Kimpton, C. P., et al. (1989) J. Virological Methods 24:335–346.

Lion, T., et al. (1990) Analytical Biochem. 188:335–337.

Musiana, M., et al. (1990) Histochemistry 94:21–25.

Permeen, A. M. Y. et al. (1990) Jour. Virological Methods 27:261–268.

Riley, L. K., et al. (1990) Jour. Clin. Microbio. vol. 28, No. 6, pp. 1465–1468.

Schafer, R., et al. (1988) Nucleic Acids Research, vol. 16, No. 19., pp. 9344–9345.

Tautz, D., et al. (1989) Chromosoma 98:81–85.

Zischler, H., et al. (1989) Hum. Genet. 82:227–233.

Singleton, P. and D. Sainsbury "Dictionary of Microbiology and Molecular Biology", 2nd Ed. Wiley-Interscience pp. 498, 539–540.

Alberts, B. et al. "Molecular Biology of the Cell" Garland, 1983 pp. 4–5.

Gray, P. "The Dictionary of the Biological Sciences", 1967 p. 296.

Chambers Dictionary of Science and Technology, Revised Edition p. 683.

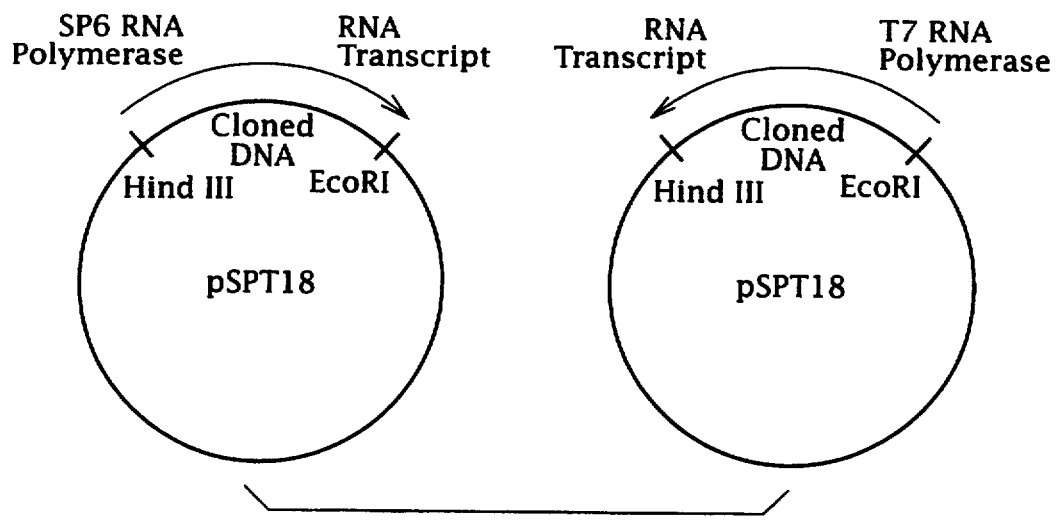
FIG. 4
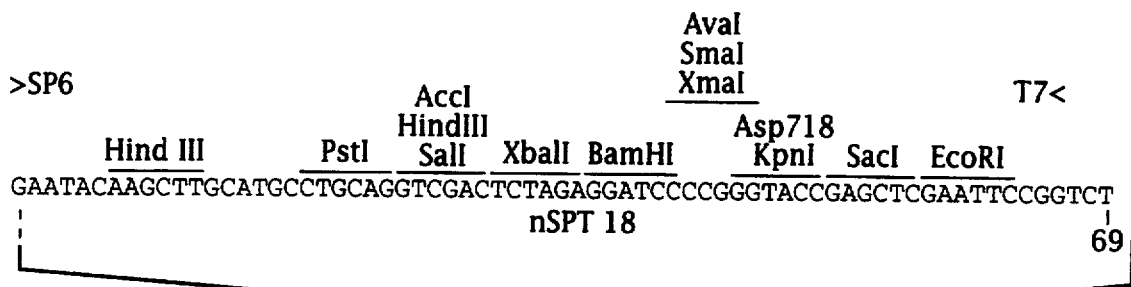
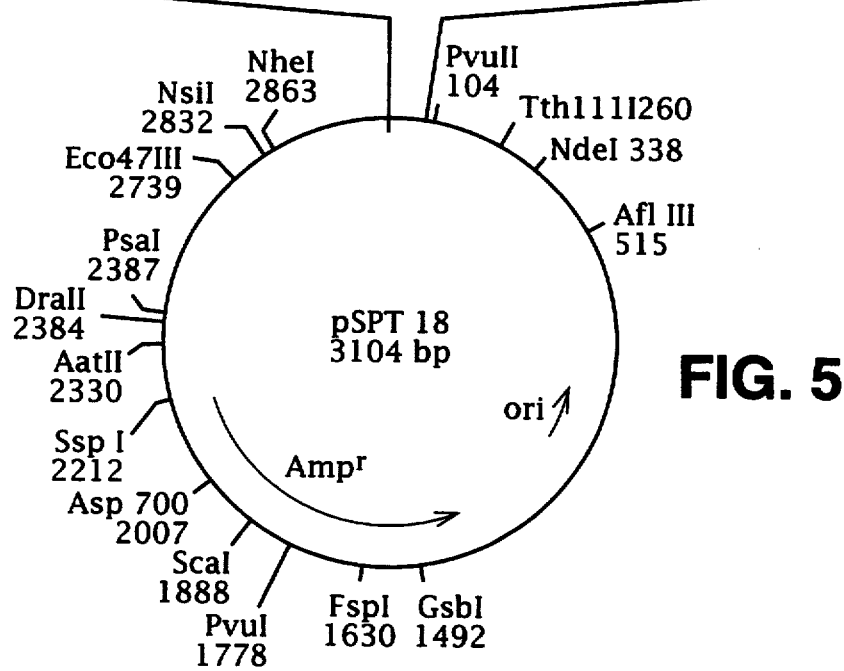
FIG. 5

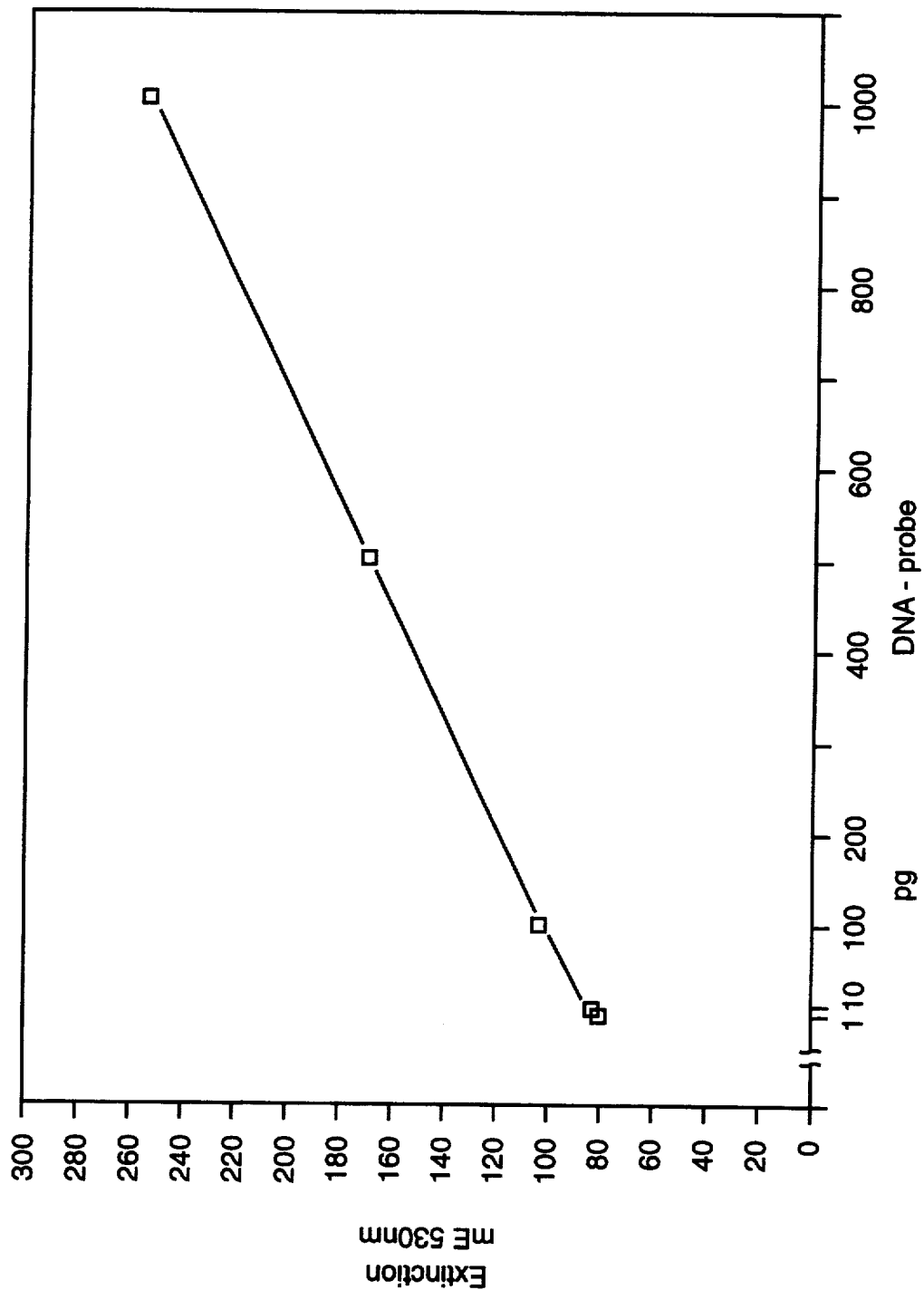

FIG. 7

DNA Sequence (7A) and restriction map (7B) of spt 18

FIG. 7A

| | | | | | |
|---|---|---|---|---|---|
| 1 | GAATACAAGC | TTGCATGCCT | GCAGGTCGAC | TCTAGAGGAT | CCCCGGGTAC |
| 51 | CGAGCTCGAA | TTCCGGTCTC | CCTATAGTGA | GTCGTATTAA | TTTCGATAAG |
| 101 | CCAGCTGGGC | CTCGCGCGTT | TCGGTGATGA | CGGTGAAAAC | CTCTGACACA |
| 151 | TGCAGCTCCC | GGAGACGGTC | ACAGCTTGTC | TGTAAGCGGA | TGCCGGGAGC |
| 201 | AGACAAGCCC | GTCAGGGCGC | GTCAGCGGGT | GTTGGCGGGT | GTCGGGCGC |
| 251 | AGCCATGACC | CAGTCACGTA | GCGATAGCGG | AGTGTATATA | CTGGCTTAAC |
| 301 | TATGCGGCAT | CAGAGCAGAT | TGTACTGAGA | GTGCACCATA | TGCGGTGTGA |
| 351 | AATACCGCAC | AGATGCGTAA | GGAGAAAATA | CCGCATCAGG | CGCTCTTCCG |
| 401 | CTTCCTCGCT | CACTGACTCG | CTGCGCTCGG | TCGTTCGGCT | GCGGCGAGCG |
| 451 | GTATCAGCTC | ACTCAAAGGC | GGTAATACGG | TTATCCACAG | AATCAGGGGA |
| 501 | TAACGCAGGA | AAGAACATGT | GAGCAAAAGG | CCAGCAAAAG | GCCAGGAACC |
| 551 | GTAAAAAGGC | CGCGTTGCTG | GCGTTTTTCC | ATAGGCTCCG | CCCCCCTGAC |
| 601 | GAGCATCACA | AAAATCGACG | CTCAAGTCAG | AGGTGGCGAA | ACCCGACAGG |
| 651 | ACTATAAAGA | TACCAGGCGT | TTCCCCCTGG | AAGCTCCCTC | GTGCGCTCTC |
| 701 | CTGTTCCGAC | CCTGCCGCTT | ACCGGATACC | TGTCCGCCTT | TCTCCCTTCG |
| 751 | GGAAGCGTGG | CGCTTTCTCA | ATGCTCACGC | TGTAGGTATC | TCAGTTCGGT |
| 801 | GTAGGTCGTT | CGCTCCAAGC | TGGGCTGTGT | GCACGAACCC | CCCGTTCAGC |
| 851 | CCGACCGCTG | CGCCTTATCC | GGTAACTATC | GTCTTGAGTC | CAACCCGGTA |
| 901 | AGACACGACT | TATCGCCACT | GGCAGCAGCC | ACTGGTAACA | GGATTAGCAG |
| 951 | AGCGAGGTAT | GTAGGCGGTG | CTACAGAGTT | CTTGAAGTGG | TGGCCTAACT |
| 1001 | ACGGCTACAC | TAGAAGGACA | GTATTTGGTA | TCTGCGCTCT | GCTGAAGCCA |
| 1051 | GTTACCTTCG | GAAAAAGAGT | TGGTAGCTCT | TGATCCGGCA | AACAAACCAC |
| 1101 | CGCTGGTAGC | GGTGGTTTTT | TTGTTTGCAA | GCAGCAGATT | ACGCGCAGAA |
| 1151 | AAAAGGATC | TCAAGAAGAT | CCTTTGATCT | TTTCTACGGG | GTCTGACGCT |
| 1201 | CAGTGGAACG | AAAACTCACG | TTAAGGGATT | TTGGTCATGA | GATTATCAAA |

FIG. 7B

```
1251  AAGGATCTTC ACCTAGATCC TTTTAAATTA AAAATGAAGT TTTAAATCAA
1301  TCTAAAGTAT ATATGAGTAA ACTTGGTCTG ACAGTTACCA ATGCTTAATC
1351  AGTGAGGCAC CTATCTCAGC GATCTGTCTA TTTCGTTCAT CCATAGTTGC
1401  CTGACTCCCC GTCGTGTAGA TAACTACGAT ACGGGAGGGC TTACCATCTG
1451  GCCCCAGTGC TGCAATGATA CCGCGAGACC CACGCTCACC GGCTCCAGAT
1501  TTATCAGCAA TAAACCAGCC AGCCGGAAGG GCCGAGCGCA GAAGTGGTCC
1551  TGCAACTTTA TCCGCCTCCA TCCAGTCTAT TAATTGTTGC CGGGAAGCTA
1601  GAGTAAGTAG TTCGCCAGTT AATAGTTTGC GCAACGTTGT TGCCATTGCT
1651  ACAGGCATCG TGGTGTCACG CTCGTCGTTT GGTATGGCTT CATTCAGCTC
1701  CGGTTCCCAA CGATCAAGGC GAGTTACATG ATCCCCCATG TTGTGCAAAA
1751  AAGCGGTTAG CTCCTTCGGT CCTCCGATCG TTGTCAGAAG TAAGTTGGCC
1801  GCAGTGTTAT CACTCATGGT TATGGCAGCA CTGCATAATT CTCTTACTGT
1851  CATGCCATCC GTAAGATGCT TTTCTGTGAC TGGTGAGTAC TCAACCAAGT
1901  CATTCTGAGA ATAGTGTATG CGGCGACCGA GTTGCTCTTG CCCGGCGTCA
1951  ATACGGGATA ATACCGCGCC ACATAGCAGA ACTTTAAAAG TGCTCATCAT
2001  TGGAAAACGT TCTTCGGGGC GAAAACTCTC AAGGATCTTA CCGCTGTTGA
2051  GATCCAGTTC GATGTAACCC ACTCGTGCAC CCAACTGATC TTCAGCATCT
2101  TTTACTTTCA CCAGCGTTTC TGGGTGAGCA AAAACAGGAA GGCAAAATGC
2151  CGCAAAAAAG GGAATAAGGG CGACACGGAA ATGTTGAATA CTCATACTCT
2201  TCCTTTTTCA ATATTATTGA AGCATTTATC AGGGTTATTG TCTCATGAGC
2251  GGATACATAT TTGAATGTAT TTAGAAAAAT AAACAAATAG GGGTTCCGCG
2301  CACATTTCCC CGAAAAGTGC CACCTGACGT CTAAGAAACC ATTATTATCA
2351  TGACATTAAC CTATAAAAAT AGGCGTATCA CGAGGCCCTT TCGTCTCGCG
2401  CGTTTCGGTG ATGACGGTGA AAACCTCTGA CACATGCAGC TCCCGGAGAC
2451  GGTCACAGCT TGTCTGTAAG CGGATGCCGG GAGCAGACAA GCCCGTCAGG
2501  GCGCGTCAGC GGGTGTTGGC GGGTGTCGGG GCTGGCTTAA CTATGCGGCA
2551  TCAGAGCAGA TTGTACTGAG AGTGCACCAT ATCGACGCTC TCCCTTATGC
2601  GACTCCTGCA TTAGGAAGCA GCCCAGTAGT AGGTTGAGGC CGTTGAGCAC
2651  CGCCGCCGCA AGGAATGGTG CATGCAAGGA GATGGCGCCC AACAGTCCCC
2701  CGGCCACGGG CCTGCCACCA TACCCACGCC GAAACAAGCG CTCATGAGCC
2751  CGAAGTGGCG AGCCCGATCT TCCCCATCGG TGATGTCGGC GATATAGGCG
2801  CCAGCAACCG CACCTGTGGC GCCGGTGATG CCGGCCACGA TGCGTCCGGC
```

FIG. 7C

```
2851  GTAGAGGATC TGGCTAGCGA TGACCCTGCT GATTGGTTCG CTGACCATTT
2901  CCGGGTGCGG GACGGCGTTA CCAGAAACTC AGAAGGTTCG TCCAACCAAA
2951  CCGACTCTGA CGGCAGTTTA CGAGAGAGAT GATAGGGTCT GCTTCAGTAA
3001  GCCAGATGCT ACACAATTAG GCTTGTACAT ATTGTCGTTA GAACGCGGCT
3051  ACAATTAATA CATAACCTTA TGTATCATAC ACATACGATT TAGGTGACAC
3101  TATA
```

FIG. 8

| Enzyme | Number of Cleavage Sites | Position of Cleavage Sites | | | | |
|---|---|---|---|---|---|---|
| Ava II | 2 | 1546 | 1768 | | | |
| Bgl I | 2 | 106 | 1528 | | | |
| Eco 31I | 2 | 71 | 1469 | | | |
| Fin I | 2 | 2699 | 2908 | | | |
| Hgi EII | 2 | 335 | 1096 | | | |
| Sph I | 2 | 17 | 2674 | | | |
| Apy I | 3 | 543 | 664 | 677 | | |
| Ban II | 3 | 56 | 2750 | 2764 | | |
| Bbe I | 3 | 2688 | 2801 | 2822 | | |
| Cfr 10I | 3 | 1488 | 2821 | 2830 | | |
| Dra I | 3 | 1274 | 1293 | 1985 | | |
| Eae I | 3 | 1796 | 2702 | 2832 | | |
| Eco 57I | 3 | 1063 | 2075 | 2977 | | |
| Eco RII | 3 | 541 | 662 | 675 | | |
| Gdi II | 3 | 1796 | 2701 | 2832 | | |
| Hae I | 3 | 528 | 539 | 991 | | |
| Mme I | 3 | 730 | 914 | 2966 | | |
| Nar I | 3 | 2685 | 2798 | 2819 | | |
| Tth 111II | 3 | 1105 | 1112 | 1144 | | |
| Apa LI | 4 | 331 | 829 | 2075 | 2572 | |
| Bsp HI | 4 | 1235 | 2243 | 2348 | 2742 | |
| Aha II | 5 | 1945 | 2327 | 2685 | 2798 | 2819 |
| Ban I | 5 | 46 | 1356 | 2684 | 2797 | 2818 |
| Fok I | 5 | 201 | 1374 | 1555 | 1842 | 2485 |
| Mae I | 5 | 32 | 1010 | 1263 | 1598 | 2864 |
| Mae II | 5 | 266 | 1218 | 1634 | 2007 | 2327 |
| Nsp I | 5 | 17 | 152 | 519 | 2436 | 2674 |
| Rsa I | 5 | 48 | 323 | 1888 | 2564 | 3026 |
| Sec I | 5 | 41 | 42 | 675 | 2698 | 2704 |

Enzymes which do not cut

| | | | | |
|---|---|---|---|---|
| Afl II | Apa I | Asu II | Avr II | Bal I |
| Bbv II | Bcl I | Bgl II | Bsm I | Bsp MII |
| Bss HII | Bst EII | Bst XI | Cla I | Dra III |
| Eco Rv | Eco R124 | Esp I | Hpa I | Mlu I |
| Nco I | Not I | Nru I | Nsi I | Pfl MI |
| Pma CI | Ppu MI | Rsr II | Sac II | Sau I |
| Sfi I | Sna I | Sna BI | Spe I | Spl L |
| Stu I | Sty I | Xho I | Xma III | |

PROCESS FOR THE HIGHLY SPECIFIC DETECTION OF NUCLEIC ACIDS IN SOLID

This application is a continuation of application Ser. No. 919,506, filed Jul. 24, 1992, abandoned which was a continuation of Ser. No. 709,071, filed May 30, 1991, now abandoned which was a continuation of Ser. No. 296,444, filed Jan. 12, 1989, abandoned.

The present invention is concerned with a process for the detection of nucleic acids of definite sequence by hybridization with two single-stranded nucleic acid probes present in the same solution phase complementary to different regions of the nucleic acid to be detected, one nucleic acid probe serving as detector probe and containing as labelling at least one hapten bound via a chemical linkage and the other nucleic acid probe serving as capturing probe and being bound to a solid matrix.

One of the most used molecular-biological techniques is the DNA/DNA, RNA/RNA or RNA/DNA hybridization for the detection of homologous nucleic acid sequences. For this purpose, the nucleic acid to be detected is denatured and fixed on to a filter, whereupon the detection is carried out via the hybridization with a labelled complementary nucleic acid probe. The hybridization results in the formation of hybrid double strands consisting of individual strands of complementary sequence to the nucleic acid to be detected and of the nucleic acid probe. The detection then takes place via the labelling of the complementary nucleic acid probe. For labelling the probe, hitherto there was mostly used the incorporation of radioactively derivatised desoxyribonucleoside triphosphates. The detection of the hybrids then took place by way of an autoradiograph. Because of the problems of disposing of radioactive compounds, as well as the further risks involved in handling radioactive compounds, a non-radioactive type of labelling of nucleic acid probes was developed. This labelling took place, for example, via the biotin/(strept)avidin binding or a hapten/anti-hapten-antibody binding and labelling enzyme conjugates coupled thereon. In this case, the detection of the hybridization product took place by the determination of the enzymatic activity of the labelling enzyme via coupled coloured material systems. However, the non-radioactive systems, with the exception of the biotin/(strept)avidin system, display a substantially smaller detection sensitivity in comparison with radioactive systems, namely, a reduction of the sensitivity by at least a factor of 10. In the case of the biotin/(strept)avidin system, in the case of direct detection of nucleic acids by means of biotin-labelled nucleic acid probes, the achievable detection sensitivity lies in the same range as in the case of radioactive labelling, namely, in the detection of 1 to 0.1 pg. DNA in the dot blot and in the detection of "single copy" genes in the genomic blot in 10 to 1 μg. genomic DNA fragments. However, the detection sensitivity in coupled detection systems in solution lies distinctly lower even in the case of using the biotin/(strept)avidin system.

However, a great disadvantage of the previously used filter binding of the nucleic acid sequences to be detected is due to the face that, because of the adsorptive binding of the single-stranded nucleic acids on the filter, only an incomplete hybridization with the nucleic acid probe can take place since a considerable part of the nucleic acid present is inaccessible for the hybridization and, under certain circumstances, only 10 to 30% of the total nucleic acid is available for the actual detection. In addition thereto, the precise detection is made difficult by non-specific binding of the labelled nucleic acid probe on the filter.

Therefore, published Federal Republic of Germany Patent Specification No. 35 46 312 describes a coupled detection process in which, for the detection of nucleic acids in solution, working is carried out with two nucleic acid probes, one probe serving as detector probe and the other as capturing probe.

The complex formed from the nucleic acid to be detected and the capturing and detector probes is hereby isolated, via a component coupled on to a capturing probe, which can function as a component in an affinity pair, and via the other component of the affinity pair adsorptively bound to the matrix, from the hybridization mixture and identified via the detector probe which contains an indicator material. The detection sensitivity lies in ng. range. As indicator materials for the detector probe in such a sandwich hybridization, there are mentioned, inter alia, immunologically detectable haptens. However, haptens and the corresponding anti-hapten-antibodies display a considerably smaller binding constant ($K = 2 \times 10^8$ mol$^{-1}$ to $7 \times 10^9$ mol$^{-1}$; Hunter et al., J. Immunol., 129, No. 3, 1165/1982) than is the case with biotin/(strept)avidin ($K = 10^{15}$ mol$^{-1}$; N. M. Green, Adv. Protein Chem, 29, 85–133/1975; L. Chaet, Wolf, Fig., Arch. Biochem. Biophys., 106, 1–5/1964) (about a factor of 105 lower). However, the utilization of the biotin/(strept)avidin exchange action for the detection reaction has the decisive disadvantage that it is very subject to disturbance since the vitamin biotin occurs in almost all biological materials.

Therefore, it is an object of the present invention to provide a highly sensitive non-radioactive detection possibility for nucleic acids in solution which avoids the above-mentioned disadvantages.

Thus, according to the present invention, there is provided a process for the detection of nucleic acids of definite sequence by hybridization with two single-stranded nucleic acid probes present in the same solution phase complementary to different regions of the nucleic acid to be detected, one nucleic acid probe serving as detector probe and containing as labelling at least one hapten bound via a chemical linkage and the other nucleic acid probe serving as capturing probe and being bound to a solid matrix, wherein, as hapten, a steroid is used which on at least one position of the detector probe, which does not participate in the hydrogen bridge formation with the nucleic acid to be detected, is covalently bound via a bridge of at least four atoms, the nucleic acid to be detected, present in solution, is incubated with the detector probe and the capturing probe in any desired sequence, whereby the binding of the capturing probe on the matrix with the nucleic acid to be detected is brought about before, during or after the incubation, the remaining solution is separated off from the matrix-bound complex of capturing probe, nucleic acid to be detected and detector probe and the complex detected via an anti-hapten antibody which is labelled.

Hitherto, it was thought that because of the large binding constant of the biotin/(strept)avidin exchange action ($K = 10^{15}$ mol$^{-1}$), all alternative, specific exchange actions with smaller binding constants would be less sensitive. Furthermore, the biotin/(strept)avidin exchange action appeared to be favoured by the presence of four biotin binding points on (strept)avidin. Therefore, previously in the non-radioactive nucleic acid detection systems, the biotin/(strept)avidin exchange actions were preferably used for the detection reaction.

However, according to the present invention, it is possible to detect nucleic acids specifically with at least the same sensitivity as with biotin-streptavidin, the selectivity thereby being increased so that not only for the matrix binding but also for the detection reaction, alternative, specific exchange action principles are used which, in each case, display a high nucleic acid detection sensitivity. The binding of the nucleic acid to be detected in the absence of either capturing probe or detector probe does not lead to a detection signal.

An important advantage of the process according to the present invention is the fact that in the case of the determination, significantly less non-specific bindings occur and, therefore, the exactitude of the determination is increased and the non-specific background is lowered.

The sequence of the binding of the detector and capturing probe to the nucleic acid to be detected, as well as the matrix binding of the capturing probe, is as desired. Thus, it is, inter alia, possible first simultaneously to incubate the nucleic acid to be detected with the detector probe and the capturing probe and then to bind the complex of the three nucleic acids to the matrix. Another possibility is the binding of the capturing probe to the matrix and simultaneously but spatially separate the binding of the nucleic acid to be detected to the detector probe and subsequently incubating the complex of nucleic acid to be detected and detector probe with the matrix-bound capturing probe. The capturing probe can also first be bound to the matrix and then, in the same reaction vessel be incubated with the nucleic acid to be detected and the detector probe. Any other sequence of the incubation of the nucleic acid and of the matrix is also suitable.

In a preferred embodiment of the present invention, digoxigenin or digoxin are used as the steroid. Surprisingly, these two steroids show, as haptens, the same high sensitivity in the detection of nucleic acids as the biotin/(strept)avidin system, although the K—values of the binding of these steroids to the corresponding antibody is lower by a factor of about $10^5$ than in the case of the biotin/(strept)avidin system and, in addition, (strept)avidin has four binding points for biotin.

Therefore, the sensitivity achieved according to the present invention in the coupled detection system is at least comparable with the sensitivities which can be achieved in the case of using the biotin/(strept)avidin system and less subject to disturbance with regard to non-specific binding.

The length of the bridge via which the hapten is bound to the detector probe can be from 4 to 32 atoms. The bridge is hereby built up of molecules which contain the atom carbon, oxygen, sulphur and/or nitrogen. A greater chain length is admittedly possible but no longer meaningful since an impairment of the detection sensitivity is thereby to be reckoned with. In a preferred embodiment of the present invention, the hapten is bound to the detector probe via a bridge of 11 to 16 atoms in length. The bridge preferably contains more hydrophilic than hydrophobic groupings.

In a preferred embodiment of the present invention, the bridge is linear. In a further preferred embodiment, the bridge is a branched chain and contains, at least on one chain end, a hapten molecule. By means of the presence of several hapten molecules on a branched chained bridge, the detection sensitivity can be additionally strengthened. A preferred hapten-labelled nucleoside triphosphate is illustrated in FIG. 1 of the accompanying drawings with two different preferred bridge chain lengths.

The binding of the hapten via the bridge to the detector probe is possible not only via a terminal or non-terminal phosphate group but also a ribose residue or a base of the nucleic acid probe. However, the binding of the hapten via the bridge must take place in such a manner that the hydrogen bridge formation between the two complementary nucleic acid strands is not impaired. The hapten is preferably bound via the bridge to a base or to a ribose residue of the detector probe.

It is especially preferred to bind the hapten via the bridge to the $C_5$-position of uracil or cytosine, the $C_8$-position of adenine or guanine or to the 2'-position of the ribose of the detector probe.

The connection of steroid hapten and bridge is preferably an ester, amide or ether bond.

The capturing probe can be coupled to the solid matrix in any desired manner. Thus, coordinate, adsorptive and covalent bondings are possible. However, the binding can also take place via a binding system.

In a preferred embodiment, the capturing probe is bound to the solid matrix coordinatively or covalently via a binding system. Such a binding system consists of two components, one component thereby being bound to the matrix adsorptively, coordinatively or covalently and the second component being bound to the capturing probe. By means of the binding of the two components of the binding system, the capturing probe is simultaneously coupled to the solid matrix. Appropriate binding systems include, for example the biotin/(strept)avidin system, the hapten-antihapten-antibody systems, as well as complementary nucleic acid sequences.

In a preferred embodiment, one component of the binding system is bound via a bridge of at least 4 atoms length to at least one position of the capturing probe which does not participate in the hydrogen bridge formation with the nucleic acid to be detected.

In a further preferred embodiment, the two components of the binding system are a hapten and an anti-hapten-antibody, with the proviso that the hapten is one different from the labelling of the detector probe and the anti-hapten-antibody does not cross-react with the labelling hapten of the detector probe.

In yet a further preferred embodiment, the two components of the binding system are biotin and (strept)avidin or oligo- or poly d(C) and oligo- or poly d(G). If, as binding system, there are used oligo- or poly d(C)/oligo- or poly d(G), it is further preferred when one of the two components is present directly in the 5'- or 3'-end of the capturing probe.

As solid matrix there can be used any desired material to which the capturing probe or a component of the binding system can be fixed adsorptively, coordinatively or covalently. As solid matrix, there is preferably used a nitrocellulose filter, nylon filter, plastic, Plexiglass or nitrocellulose- or nylon-coated plastic or Plexiglass. In an especially preferred embodiment, as solid matrix there is used the wall of a reaction vessel which can be, for example, a polyethylene test tube, a microtitre plate or a cuvette, in which case a further advantage of the present invention is shown in that the detection via a colour reaction can be carried out directly in the reaction vessel by measurement of the extinction or adsorption at an appropriate wavelength.

The hybridization of the detector and capturing probe with the nucleic acid to be detected takes place in solution at a temperature which is selected dependent upon the length of the nucleic acid probe and the melting temperature of the hybrids to be expected resulting therefrom.

The detection of the complex formed after the hybridization and matrix formation takes place by way of the detection of hapten-labelled, complex-bound detector probe by the binding of anti-hapten-antibodies and anti-hapten-antibody fragments, which are in turn labelled, with which the complex is incubated.

The labelling of the anti-hapten-antibody directed against the hapten of the detector probe or of a fragment takes place in known manner, enzyme labelling, radioactive labelling, fluorescent labelling or (bio)luminiescent labelling being preferred. An enzyme labelling is especially preferably used in which case, as labelling enzyme, alkaline phosphatase, peroxidase or $\beta$-galactosidase are, in turn, preferably used. The determination of the catalytic activity of the labelling system is preferably carried out via a redox system. For this purpose, leuko systems are especially preferred. The determination most preferably takes place via indigoid systems as oxidisable compounds and tetrazolium salts as oxidation agents.

In a preferred embodiment, as labelling enzyme there is used alkaline phosphatase, the determination being carried out via the redox system X-phosphate/nitro blue tetrazolium. X-Phosphate is hereby a trivial name for 5-bromo-4-chloro-3-indolyl phosphate, and nitro blue tetrazolium is the compound 3,3'-(3,3'-dimethoxy-4,4'-biphenylene)-bis-[5-phenyl-2-(4-nitrophenyl)-terazolium chloride]. Alkaline phosphatase cleaves the chromogenic substrate, in this case X-phosphate, which, due to the splitting off of the phosphate and oxidation, forms a blue, sparingly-soluble dimer, in which case the tetrazolium compound is simultaneously reduced to an also blue, sparingly soluble formazane. This redox reaction is illustrated in FIG. 2 of the accompanying drawings.

The detection of the other appropriate determination systems is carried out according to known methods.

Various methods can be used for the synthesis of single-stranded nucleic acid probes which are labelled with a hapten via a bridge.

1. In the case of the phage-RNA polymerase-catalysed "transcription" methods (J. Mol. Biol., 166, 477/1983), the ribonucleic acid is derivatized during the desoxyribonucleic acid-dependent ribonucleic acid synthesis. As phage-coding RNA polymerases, there are used, for example, phage SP6-, T7- or T3-coding enzymes. For these methods, there are used double-stranded desoxyribonucleic acids which contain SP6, T7 or T3 promoters. By means of the addition of SP6-, T7- or T3-RNA polymerase and all four types of ribonucleoside triphosphates, there is formed, starting from the homologous promoter, the ribonucleic acid strand, the transcript, complementary to the codogenic desoxyribonucleic acid strand. The four ribonucleoside triphosphate types provided as substrate are thereby incorporated. Up to four of these triphosphate types are partly or completely derivatized by coupling of a steroid via a bridge so that, in the case of the ribonucleic acid synthesis, this steroid is also incorporated. In the case of digoxigenin/digoxin labelling, digoxigenin/- digoxin-labelled ribonucleotides are used and in the case of biotin labelling, biotin-labelled ribonucleotides are used.

2. For the "reverse transcription" method, the starting material is single-stranded RNA. Retrotranscription with reverse transcriptase leads to the incorporation of hapten-labelled nucleotides into the complementary DNA strand. As reverse transcriptases, there are used, for example, virus AMV- or Mo-MLV-coding enzymes. A DNA/RNA hybrid hemi-labelled in the DNA strand results. The non-labelled RNA strand is selectively digested by alkaline hydrolysis or by treatment with RNase H.

In the case of digoxigenen/digoxin labelling, there are used digoxigenin/digoxin-labelled desoxyribonucleotides and in the case of biotin labelling there are used biotin-labelled desoxyribonucleotides.

3. In the case of the "exonuclease III" method, the starting material is double-stranded DNA, one of the two strands of which has been labelled via primer-dependent incorporation of hapten-derivatized nucleotide by means of DNA polymerase, for example Klenow enzyme, phage-coding T4 or T7, DNA polymerase or DNA polymerase from *Thermus aquaticus*. The resulting hemi-labelled double-stranded DNA is cleaved with two different Class II restriction endonucleases, one of which produces a fragment end with 5'-overhanging individual strand ends and the other fragment ends with 3'-overhanging individual strand ends. The choice of the endonucleases is such that the 5'-overhanging individual strand end is associated with the hapten-labelled strand, whereas the 3'-overhanging individual strand end is associated with the the unlabelled strand. By means of subsequent breakdown with exonuclease III, with high preference there is only broken down the non-labelled DNA strand, the 3'-end of which is recessive, i.e. not overhanging. 3'-Overhanging fragment ends are hydrolysed substantially more slowly with exonuclease III. The remaining complementary individual strand is hapten-labelled.

4. In the case of the "lambda exonuclease" method, the starting material is a double-stranded DNA, one of the two strands of which is labelled via primer-dependent incorporation of hapten-derivatized nucleotides by means of DNA polymerase, for example Klenow enzyme, phage-coding T4 or T7 DNA polymerase, DNA polymerase from *Thermus aquaticus*. As primers there are used 5',3'-dephosphorylated oligonucleotides or primers otherwise protected on the 5'-end against digestion with lambda exonuclease. Alternatively, protected primers can be obtained by folding back of 3'-end standing, inversely repetitive sequences in the single-stranded DNA which are separated from one another by at least 5 bases (terminal "loops" with internal 3'-OH ends).

Since the resulting hemi-labelled double-stranded DNA only has phosphorylated 5'-fragment ends in the unlabelled strand, with high preference only the labelled strand is broken down by subsequent reaction with lambda exonuclease. Lambda exonuclease has a high preference for phosphorylated 5'-fragment ends. Hydroxylated 5-fragment ends are hydrolyzed substantially more slowly. The remaining complementary single strand is hapten-labelled.

5. In the case of the "nick translation" method, the starting materials are double-stranded DNA fragments. After formation of a nick specifically in a strand by, for example phage F1 protein A and subsequent exchange of hapten-labelled nucleotides by *Escherichia coli* DNA polymerase I, the nick-containing strand is labelled. The resulting hemi-labelled double-stranded DNA is further treated as in 1. with two different class II restriction endonucleases and exonuclease III.

Descriptions for methods 1 to 5 are to be found in T. Maniatis et al., Molecular Cloning (1982), Cold Spring Harbor Laborazory, Cold Spring Harbor, New York; C. Kessler, Enzymes in Genetic Engineering, Ullmann's Encyclopedia of Industrial Research, Vol. A9, pub. VCH Verlagsgesellschaft Weinheim, 1987, pp. 341–530.

6. In the "photochemical" method (Nucl. Acids Res., 13, 745–761/1985), the nucleic acid probe is irradiated in the presence of photo-digoxigenin (FIG. 3) with visible light with an ultra-violet component. With the splitting off of nitrogen ($N_2$), there results a nitrene radical which binds covalently to the nucleic acid.

7. For the "chemical" method, in the scope of the oligonucleotide synthesis according to the phosphite triester method, besides the protected nucleoside phosphoramidites (dA/dG/dC/dT), there are used protected nucleoside phosphoramidites modified with substitutable amino functions (dA/dG/dC/dU) for the precise incorporation into the oligo-desoxyribonucleotide single strand. The modification of dC/dU preferably takes place in the 5-position of the pyrimidine ring and that of dA/dG preferably in the 8-position of the purine molecule.

Single-stranded oligo-desoxyribonucleotides modified on the nucleobases with substitutable amino functions resulting after conclusion of the synthesis cycles and removal of the protective groups can be labelled with appropriate haptens. Such haptens are steroids and preferably digoxigenin or digoxin, i.e. the labelling takes place by reaction of the oligo-desoxyribonucleotide with the appropriately activate esters, amides or ethers of the haptens, preferably their N—hydroxysuccinimide esters.

In a preferred embodiment of the present invention, hapten-labelled nucleic acid probes are used, the hapten of which has been incorporated into the nucleic acid probe enzymatically with the help of RNA polymerase, DNA polymerase, exonucleases or reverse transcriptases and appropriate hapten-modified desoxy- or ribonucleoside triphosphate substrates.

In a further preferred embodiment of the present invention, hapten-labelled nucleic acid probes are used, the hapten of which has been incorporated into the nucleic acid probe photochemically with the help of photo-haptens and in a third preferred embodiment, nucleic acid probes are used, the hapten of which has been incorporated into the nucleic acid probe chemically in the scope of the oligo-desoxyribonucleotide synthesis by incorporation of protected nucleoside phosphoamidites modified with substitutable amino functions and, after removal of the protective groups, by reaction of the modified oligo-desoxyribonucleotide with active esters, amides or ethers of the haptens.

The following Examples are given for the purpose of illustrating the present invention, reference thereby being made to the accompanying drawings, in which:

FIG. 4 shows the preparation of an RNA transcript according to the SP6 or T7 RNA polymerase-catalysed transcription method with the plasmid pSPT 18;

FIG. 5 shows the plasmid pSPT 18;

FIG. 6 shows the evaluation of the colour formation reaction of a nucleic acid detection according to the present invention; and, FIGS. 7A, 7B and 7C shows the DNA sequence of pSPT18.

FIG. 8 shows the restriction card of pSPT18.

EXAMPLE 1

Figure 1:
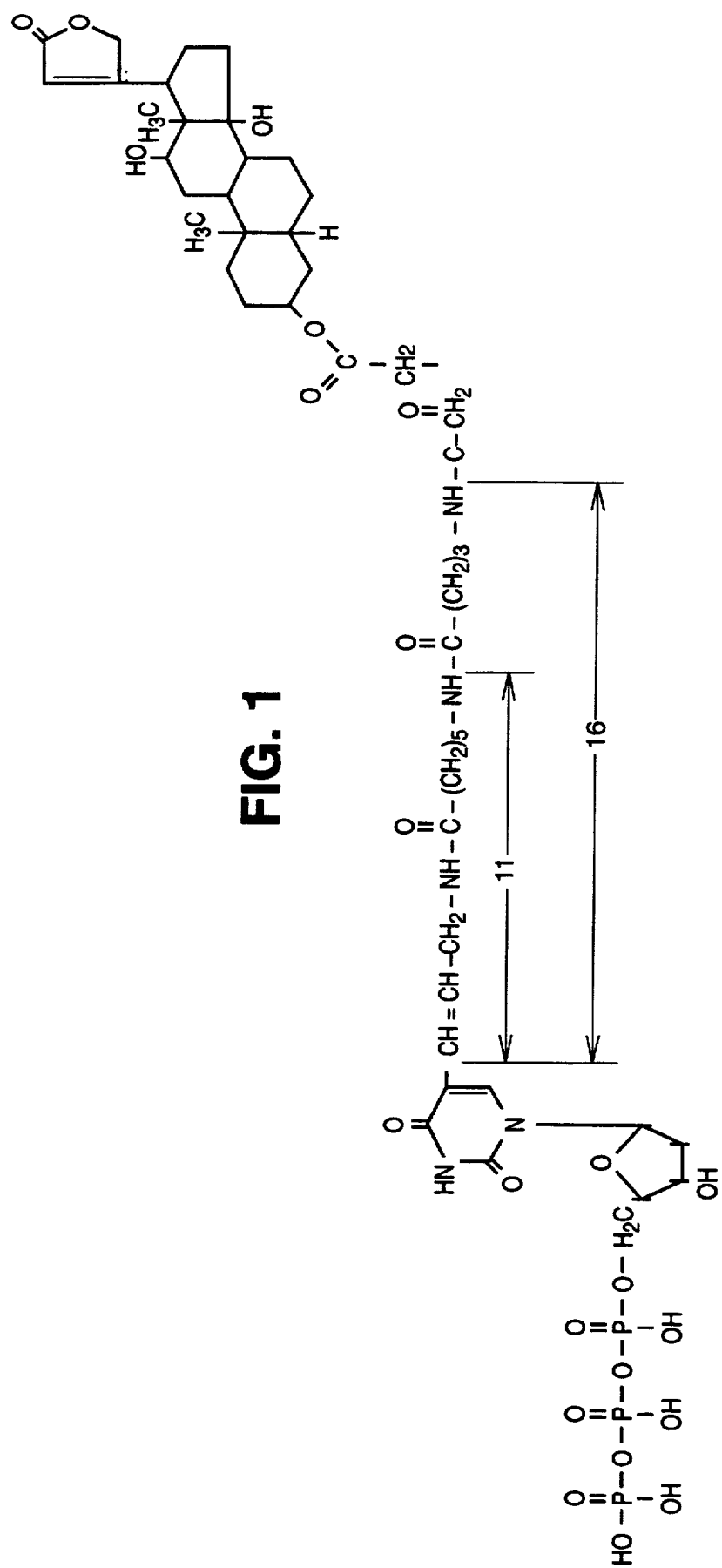
FIG. 1 shows a deoxyuridine triphosphate labelled with digoxigenin via a bridge of either 11 or 16 atoms length.
Figure 2:
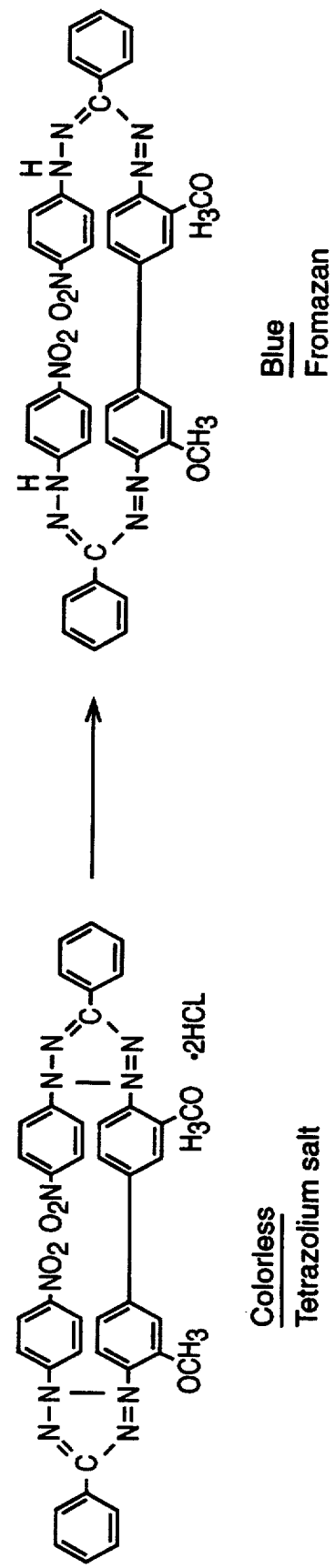
FIGS. 2A and 2B shows the colour-forming redox reaction of the system X-phosphate/nitro blue tetrazolium in the case of the action of alkaline phosphatase.
Figure 2A:
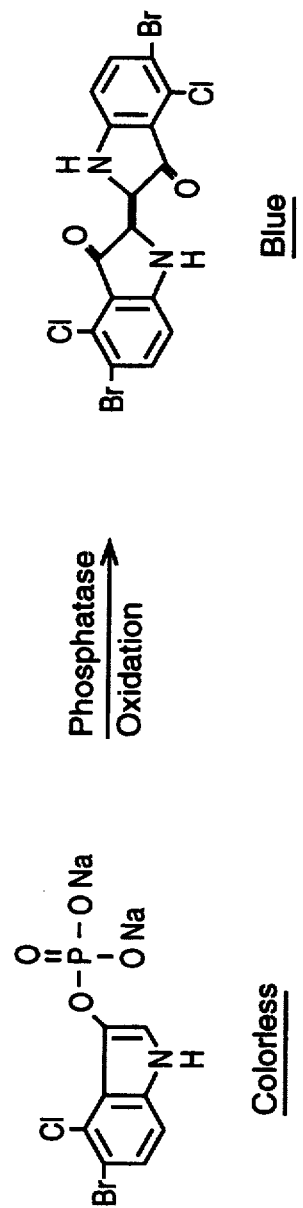
Figure 3:
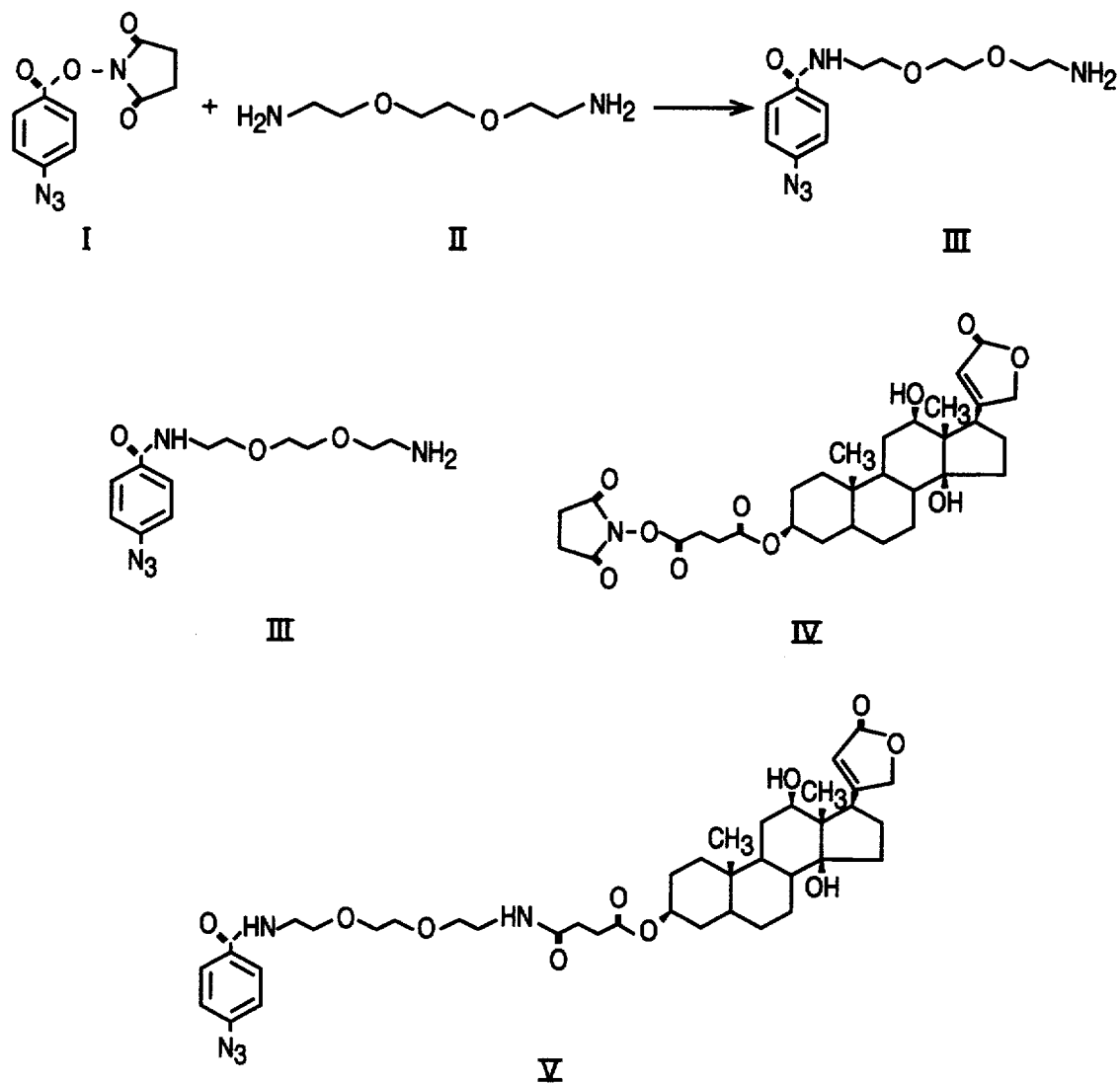
FIG. 3 shows schematically the preparation of photo-digoxigenin.

Tetralithium digoxigenin-O-succinyl-[5-(amidoallyl)-2'-2'-desoxyuridine-5'-triphosphate] (Dig-4-dUTP)

$C_{39}H_{52}O_{21}N_3P_3Li_4$ (M.W. 1019.5)

200 mg. Digoxigenin-O-succinyl-N-hydroxysuccinimide ester (0.34 mMole) are dissolved in 7 ml. dimethylformamide and a solution of 186 mg. tetralithium 5-allylamino-2'-desoxyuridine-5'-triphosphate (0.34 mMole) in 6 ml. of water added thereto. 62 ml. 0.1M sodium borate buffer (pH 8.5) are added to the reaction mixture which is then stirred overnight for about 15 hours at ambient temperature.

After this time, there is observed paper electrophoretically (0.05M citrate buffer; pH 5.0) under ultra-violet light, besides unreacted 5-allylamino-dUTP, a somewhat deeper running spot of the desired product. Purification takes place in the manner described in Example 9. Yield: 130 mg (37% theory).

UV spectrum (phosphate buffer; pH 7.0): maxima 220 nm, 290 nm.

EXAMPLE 2

Digoxigenin-O-succinyl-ε-amidocapronic acid $C_{33}H_{49}O_9N$ (M.W. 603.8)

In a 250 ml. round-bottomed flask, 5 g. digoxigenin-O-succinyl-N-hydroxysuccinimide ester (8.5 mMole) are dissolved in 150 ml. dimethylformamide and a suspension of 1.12 g. 6-aminocapronic acid (8.5 mMole) and 1.2 ml. triethylamine in 20 ml. dimethylformamide added thereto. The reaction mixture is magnetically stirred overnight, a homogeneous solution thereby gradually being formed. After this time, according to thin layer chromatography (silica gel; ethyl acetate/petroleum ether(ethanol 1:1:1 v/v/v; detection spraying with a mixture of 10 ml. glacial acetic acid+0.2 ml. concentration sulphuric acid+0.1 ml. anisaldehyde and heating to 120° C. up to the achievement of blue-black spots; $R_f$ about 0.7; $R_f$ digoxigenin-OSu ester about 0.85) the reaction is practically complete.

The dimethylformamide is completely distilled off in a vacuum and the remaining oil is dissolved in 50 ml. of water with the addition of a concentration aqueous solution of ammonia. The "free" digoxigenin-amidocapronic acid is then separated out by the addition of 225 ml. aqueous citric acid solution (100 g. citric acid/liter). The resinous viscous mass is solidified by trituration with water. It is filtered off with suction, washed repeatedly with water and finally dried over phosphorus pentoxide under oil pump vacuum. Yield: 3.45 g. (68% of theory).

EXAMPLE 3

Digoxigenin-O-succinyl-ε-amidocapronic acid N-hydroxysuccinimide ester $C_{37}H_{52}O_{11}N_2$ (M.W. 700.8)

In a 100 ml. round-bottomed flask, 3.45 g. digoxigenin-O-succinyl-ε-amidocapronic acid (5.7 mMole) are dissolved in 20 ml. anhydrous dimethylformamide and successively mixed with 0.7 g. N-hydroxysuccinimide (6 mMole), as well as 1.3 g. dicyclohexylcarbodiimide (6.3 mMole). The reaction mixture is stirred overnight at ambient temperature, the next day filtered off from precipitated dicyclohexylurea and the dimethylformamide stripped off under oil pump vacuum. The oil remaining behind is taken up in 20 ml. ethyl acetate and stirred into about 150 ml. ice-cold ($-20°$ C.) petroleum ether. The separated initially still resinous-viscous product is repeatedly triturated with ice-cold dry petroleum ether until it becomes solid. After drying in a vacuum over phosphorus pentoxide, there are obtained 3.35 g. of product (84% of theory).

Elemental analysis: calc.: C 63.4%; H 7.5%; N 4.0%; found: 63.1%; 7.7%; 4.07%.

EXAMPLE 4

Tetrasodium digoxigenin-O-succinyl-ε-amidocaproyl-[5-(amidoallyl)-2'-desoxyuridine-5'-triphosphate]

(Dig-11-dUTP)

$C_{45}H_{63}O_{22}N_4P_3Na_4$ (M.W. 1196.7)

260 mg. Digoxigenin-O-succinyl-ε-amidocapronic acid N-hydroxysuccinimide ester (0.37 mMole) are dissolved in 7 ml. dimethylformaide and added to a solution of 200 mg. tetralithium 5-allylamino-2'-desoxyuridine-5'-triphosphate (0.37 mMole) in 6 ml. of water. 62 ml. 0.1M sodium borate buffer (pH 8.5) are added to the mixture and then stirred overnight (about 15 hours) at ambient temperature.

In the paper electrophoresis (0.05M citrate buffer; pH 5.0) there is observed after this time, in ultraviolet light, besides some unreacted allylamino-dUTP, a somewhat deeper running spot of the desired compound (alternatively: thin layer chromatography on silica gel; elution agent isobutyric acid/concentrated aqueous ammonia solution/water=66:1:33 v/v/v; detection in ultra-violet light or spraying with anisaldehyde reagent (see Example 2); $R_f$ values: 5-allylamino-dUTP=0.2; Dig-amidocapronic acid OSu ester=0.7; Dig-11-dUTP=0.45).

For purification, the reaction mixture is evaporated under oil pump vacuum to a solid residue which is taken up in 200 ml. of water and applied to an ion exchanger column (DEAE-Sephadex A25, $HCO_3^-$ form, column dimensions 1.5×30 cm.). After application, the column is briefly washed with water then eluted with a gradient of, in each case, 1 liter of water to 0.4M triethylammonium bicarbonate (TEAB) (pH 8). The fractions containing the pure product are combined, concentrated in a vacuum and freed from excess TEAB by repeated evaporation with methanol, after which there is no longer a small of free triethylamine. The contents of the reaction vessel are taken up in a few ml. of water, the solution is passed over a short cation exchange column of DOWEX 50 WS8 (1×10 cm.) in the Na+ form, the column is washed with water until the wash water is free of ODE (measurement of ultra-violet light at 240 nm) and concentrated in a vacuum to about 20 ml. After lyophilization, there are obtained 200 mg. (45% of theory) of Dig-11-dUTP-Na4 in the form of a white powder.

Analysis: water determination: 7.9%.

Elementary analysis (taking into account the water content): calc.: C 41.8%; H 5.3%; N 4.3%; P 7.2%; found: 41.08%; 5.35%; 4.7%; 7.1%.

UV spectrum (phosphate buffer; pH 7.0): maxima: 220 nm, 290 nm.

EXAMPLE 5

Digoxigenin-O-succinyl-γ-amidobutyric acid $C_{31}H_{45}O_9N$ (M.W. 575.8)

The compound is prepared by reacting 3 g. digoxigenin O-succinyl-N-hydroxysuccinimide ester (5.1 mMole) with 0.63 g. 4-aminobutyric acid (6.1 mMole) as described in Example 1 for the capronic acid derivative. After the reaction has taken place, the reaction mixture is evaporated in a vacuum, the residue is dissolved in water-methanol (20%) and applied to a cation exchanger column (Dowex 50 WX8) in the H+ form. The eluate and wash water (pH about 4) are evaporated, the greasily viscous residue remaining behind is dissolved in n-butanol and shaken out three times with water. The butanol phase contains the desired product and, after stripping off the butanol and co-distilling three times with anhydrous dimethylformamide (removal of residual water), is used directly for further working up to the corresponding N-hydroxysuccinimide ester (see Example 6).

Yield: 2.94 g. in the form of an oil.

EXAMPLE 6

Digoxigenin-O-succinyl-γ-amidobutyric acid N-hydroxysuccinimide ester $C_{35}H_{48}O_{11}N_2$ (M.W. 672.8)

2.94 g. Digoxigenin-O-succinyl-γ-amidobutyric acid (about 5.1 mMole) are reacted as oil from Example 5 with 0.62 g. N-hydroxysuccinimide (5.4 mMole) and 1.16 g. dicyclohexylcarbodiimide (5.6 mMole) in 20 ml. anhydrous dimethylformamide as described in Example 3 and worked up. The resulting hydroxysuccinimide ester is reacted as an oil, as described in Example 7, with ε-aminocapronic acid.

Yield: 3.46 g. in the form of an oil.

EXAMPLE 7

Digoxigenin-O-succinyl-γ-amidobutyryl-ε-amidocapronic acid $C_{37}H_{56}O_{10}N_2$ (M.W. 689.0)

In a 250 ml. round-bottomed flask, 0.8 g. ε-aminocapronic acid (6.2 mMole) and 0.75 ml. triethylamine are suspended in 12 ml. dimethylformamide and a solution of 3.46 g. digoxigenin-O-succinyl-γ-amidobutyric acid N-hydroxysuccinimide ester (5.1 mMole, oil from Example 6) in 90 ml. dimethylformamide added thereto. The reaction mixture is stirred overnight for about 15 hours at ambient temperature, whereafter an almost homogeneous solution is obtained. According to TLC (for conditions see Example 2), the reaction is almost quantitative.

The working up takes place as described in Example 5 (conversion into the "free" carboxylic acid by Dowex 50 chromatography, extraction with n-butanol). Besides the desired product, the butanol phase contains somewhat more polar and non-polar material and, for this reason, is purified by chromatography on silica gel 60 (column 40×3 cm.; elution agent ethyl acetate/petroleum ether 50/75/ethanol 1:1:1 v/v/v). After combining the acidic fractions and evaporating, there is obtained an oily product.

Yield: 1.48 g. (42% of theory).

EXAMPLE 8

Digoxigenin-O-succinyl-γ-amidobutyryl-ε-amidocapronic acid N-hydroxysuccinimide ester $C_{41}H_{59}O_{12}N_3$ (M.W. 785.8)

0.2 g. Digoxigenin-O-succinyl-γ-amidobutyryl-ε-amidocapronic acid (oil from Example 7; about 0.29 mMole) are reacted with 0.034 g. N-hydroxysuccinimide (0.3 mMole) and 66 mg. dicyclohexylcarbodiimide (0.32 mMole) in 8 ml. anhydrous dimethylformamide as described in Example 3 and worked up. The oily residue obtained cannot be solidified even after repeated trituration with cold petroleum ether and is, therefore, after stripping off the solvent, used directly, as described in Example 9, for reaction with 5-aminoallyl-dUTP.

Yield: 0.25 g. in the form of an oil.

EXAMPLE 9

Tetralithium digoxigenin-O-succinyl-γ-amidobutyryl-ε-amidocaproyl-[5-(amidoallyl)-2'-desoxyuridine-5'-triphosphate]

(Dig-16-dUTP)

$C_{49}H_{70}O_{23}N_5P_3Li_4$ (M.W. 1217.7)

250 mg. Digoxigenin-O-succinyl-γ-amidobutyryl-ε-amidocapronic acid N-hydroxysuccinimide ester (oil from Example 8; about 0.3 mMole) are dissolved in 7 ml. dimethylformamide and added to a solution of 210 mg. 5-allylamino-2'-desoxyuridine-5'-triphosphate tetralithium salt (0.38 mMole) in 6 ml. of water. 62 ml. 0.2M sodium borate buffer (pH 8.5) are added to the reaction mixture and this then stirred overnight for about 15 hours at ambient temperature. The course of the reaction is monitored as described in Example 4.

For purification, the reaction mixture is evaporated to a solid residue under oil pump vacuum, the residue is dissolved in about 200 ml. of water and applied to an ion exchanger column (DEAE-Sephadex A-25, Cl⁻ form; column dimensions 1.5×30 cm.). After washing with water, the column is eluted with a linear gradient of 2 liters of water to 2 liters of 0.3M lithium chloride solution. The fractions containing the pure product are concentrated in a vacuum until no more water passes over and the concentrate is subsequently precipitated by stirring in an acetone-ethanol mixture (3:1 v/v). The supernatant is centrifuged off, the solid material is washed with ethanol until free of chloride ions and then dried in a vacuum over phosphorus pentoxide/potassium hydroxide.

Yield: 250 mg. (68% of theory).

Analysis: water determination; 6.3%.

Elementary analysis (taking into account the water content): calc.: C 45.5%; H 5.7%; N 5.4%; P 7.2%; found: 45.1%; 5.6%; 5.6%; 7.0%.

UV spectrum (phopshate buffer; pH 7.0).

Maxima: 200 nm (shoulder), 289 nm.

EXAMPLE 10

Tetralithium digoxigenin-O-succinyl-ε-amidocaproyl-[5-(amidoallyl)-uridine-5'-triphosphate]

(Dig-11-UTP)

$C_{45}H_{63}O_{23}N_4P_3Li_4$ (M.W. 1148.5)

The compound is prepared by reacting 520 mg. digoxigenin-O-succinyl-ε-amidocapronic acid N-hydroxysuccinimide ester (0.74 mMole) with 416.5 mg. tetralithium 5-allylamino-UTP (0.74 mMole) analogously to Example 4. However, in a variation of Example 9, the ion exchanger chromatography took place on DEAE-Sephadex A-25 in the Cl⁻ form.

Yield: 560 mg. (66% of theory).

Analysis: water determination: 8.1%.

Elementary analysis (taking into account the water content): calc.: C 43.5%; H 5.47%; N 4.5%; P 7.47%; found: 43.1%; 5.3%; 4.5%; 7.35%.

UV spectrum (phosphate buffer; pH 7.0): corresponds to Dig-11-dUTP.

EXAMPLE 11

Tetralithium digoxigenin-O-succinyl-γ-amidobutyryl-ε-amidocaproyl-[5-(amidoallyl)-uridine-5'-triphosphate]

(Dig-16-dUTP)

$C_{49}H_{70}O_{24}N_5P_3Li_4$ (M.W. 1233.7)

The compound is prepared by reacting 250 mg. digoxigenin-O-succinyl-γ-amidobutyryl-ε-amidocapronic acid N-hydroxysuccinimide ester (0.3 mMole; obtained according to Example 8) with 214 mg. 5-allylamino-UTP tetralithium salt (0.38 mMole) analogously to Example 9.

Yield: 218 mg. (59% of theory).

Analysis: water determination=7.2%.

Elementary analysis: (taking into account the water content): calc.: C 44.45%; H 5.67%; N 5.3: P 7.0%; found: 44.3%; 5.5%; 5.3%; 7.1%.

UV spectrum (phosphate buffer; pH 7.0): corresponds to Dig-16-dUTP.

EXAMPLE 12

Preparation of N-azidobenzoyl-1,8-diamino-3,6-dioxaoctane 5.20 g. (20 mMole) Azidobenzoic acid N-hydroxysuccinimide ester (firm Pierce, D-6054 Rodgau 1) are dissolved in anhydrous ethyl acetate and mixed with 29.3 ml. (200 mMole) 1,8-diamino-3,6-dioxaoctane. The reaction mixture is stirred in the dark for 20 hours at 20° C. The solvent is removed in a vacuum and the oily residue is dissolved in 300 ml. of water. The product is extracted from the aqueous phase with 2 liters of toluene in a perforator, the apparatus being wound round with aluminium foil. The extraction is finished after about 16 hours. The organic phase is freed from solvent in a vacuum and the product purified by preparative column chromatography on silica gel (column 80×10 cm.; eluent: chloroform/methanol/concentrated aqueous ammonium solution 65:30:5 v/v/v) and, after evaporating off the solvent, is dried in a high vacuum.

Yield: 3.2 g. (55% of theory) of a colourless, viscous oil.

EXAMPLE 13

Preparation of digoxigenin-3-hemisuccinate [N'-(4-azidobenzoyl)]-8-amino-3,6-dioxaoctylamide (photodigoxigenin)

2.93 g. (10 mMole) of the product from Example 12 are dissolved in 200 ml. anhydrous dioxan and mixed with 5.87 g. (10 mMole) digoxigenin-3-hemisuccinate N-hydroxysuccinimide ester (preparation analogous to G. C. Oliver, Jr. Brent, M. Parker, D. L. Brasfield and Ch. W. Parker, J. Clin. Invest., 47, 1035/1986). The reaction mixture is stirred for 20 hours at ambient temperature, the solvent is removed in a vacuum and the resultant product is separated off by preparative average pressure liquid chromatography (column volume: 1640 ml., Labochrom reversed phase silica HD-SIL-18-30-60, elution agent: methanol/water 7;3 v/v+1% glacial acetic acid). After collecting the appropriate fractions, the solvent is removed in a vacuum and the oily residue dissolved in dioxin. After lyophilisation and washing with 100 ml. diisopropyl ether, the product, digoxigenin-3-hemisuccinate [N'-(4-azidobenzoyl)]-8-amino-3,6-dioxaoctylamide is obtained as a colourless, slightly sticky solid material which is dried in a high vacuum.

Yield: 4.9 g. (64% of theory).
IR (acetone): 2150, 1728, 1639 cm$^{-1}$.

EXAMPLE 14

Labelling of a Nucleic Acid Probe by in vitro Transcription of RNA ("Transcription" Method)

The principle of the reaction is to be seen from FIG. 4 of the accompanying drawings. The DNA used for the labelling is inserted into the transcription vector pSPT18 (see FIGS. 5 and 7 of the accompanying drawings). The vector contains a promoter for the SP6 and a promoter for the T7 RNA polymerase. Before the labelling reaction, the DNA is linearized at a point outside of the inserted DNA sequence and of the promoters, as well as the sequences binding the promoters and the DNA sequence.

1 µg. of the linearized substrate DNA is added in a reaction vessel to 1 µl. each of a 10 mMole/liter solution of adenosine triphosphate, cytidine triphosphate and guanosine triphosphate. For that purpose, 1 µl. of a solution which contains 6.5 mMole/liter uridine triphosphate and 3.5 mMole/liter digoxigenin-11-UTP is added thereto. Digoxigenin-11-UTP is prepared in Example 10 similarly to digoxigenin-11-dUTP in Example 4: as starting material there is used allylamino-uridine salt instead of allylamino-desoxy-uridine salt.

Furthermore, there is added to the batch 2 µl. of a 10 fold concentrated buffer (Tris-HCl, 0.4 mole/liter; magnesium chloride, 60 mMole/liter; dithiothreitol, 50 mMole/liter; spermidine, 40 mMole/liter; pH 7.2), the volume is made up to 19 µl. with sterile double distilled water and finally the reaction is started by the addition of 1 µl., corresponding to 10 Units, of the RNA polymerase (SP6 or T7). After a short centrifuging, the batch is incubated at 37° C. for 1 hour. The substrate DNA is subsequently broken down for 15 minutes at 37° C. by the addition of 1 µl. DNAse I (RNAse-free), corresponding to 10 Units.

The reaction is stopped by the addition of 2 µl. of 0.2 mole/liter EDTA (pH 8.0). The digoxigenin-labelled RNA probe obtained is purified by extraction with 1 volume of phenol and by subsequent ethanol precipitation of proteins and nucleotides and finally dissolved in sterile buffer (Tris-HCl, 10 mMole/liter; EDTA, 1 mMole/liter, pH 8.0).

EXAMPLE 15

Sandwich Hybridisation of Digoxigenin- and Biotin-labelled Oligonucleotides a) Oligonucleotides used
Nucleic acid to be detected: 95 mer

```
5'GGAGTGAGCG TTACGGTAGT TGTTCTTCCA AGCAACGGTC
CAACCCAGAG CAGTACCGGA ACCGTCGGTA GCTGGCGCGC
TGTCGTATCT ACCGG
```

Capturing probe: 95 mer, 48 bases complementary to the nucleic acid to be detected

```
5'-CTGGG TTGGACCGTT GCTTGGAAGA ACAACTACCG
TAACGCTCAC TCCGCTACCA CCTGGTCCGG TCAGTACGTT
GGTGGCGCCG AAGCTCGTAT
```

Detector probe: 95 mer, 47 bases complementary to the nucleic acid to be detected

```
5'-GTACTTACGA ATCCGCTGTT GGTAACGCTG AATCCCGTTA
CGTTTTGACC GGTAGATACG ACAGCGCGCC AGCTACCGAC
GGTTCCGGTA CTGCT
``` b) Photolabelling of the oligonucleotides

To 10 µg. of capturing probe in 20 µl. of distilled water are added 20 µl. of 1 mg./ml. photobiotin (see Forster et al., Nucl. Acids Res., 13, 745–761/1985) in subdued light. The mixture is irradiated for 20 minutes in an open Eppendorf reaction vessel, while cooling with ice, with a Phillips HPLR 400 W discharge lamp at a distance of 10 cm.

After the reaction, the mixture is made up to 100 µl. with 0.1M Tris-HCl (pH 9.0), 1.0 mM EDTA and extracted twice with butan-2-ol. After the second extraction, the volume of the aqueous phase is 30 to 40 µl.

After the addition of carrier t RNA (about 1 µg.) and 1/10 volume of 3M ammonium acetate solution, it is precipitated overnight at −20° C. with 3 volumes of ethanol.

The pellet obtained after centrifuging off at 4° C. is washed with cold ethanol and dried. The labelled DNA is taken up in 10 mM Tris-HCl (pH 7.5), 0.1 mM EDTA and stored at 4° C.

The labelling of the digoxigenin takes place according to the same process. A solution of 1 mg./ml. photodigoxigenin (see Example 13) in dimethylformamide is used. 10 μl. 5M sodium chloride solution are added for the phase separation in the case of the extraction with butan-2-ol.

c) Coating of a membrane with streptavidin

The membrane Nytran 13N Schleicher & Schüll is used.

Membrane strips are cut which fit into the Schleicher & Schüll slot mutlifiltration apparatus and moistened with distilled water. Subsequently, the membrane is incubated at ambient temperature, with shaking, in 1 mg./ml. thermoRSA (prepared according to European Patent Application No. 87 117 411.6)-streptavidin for 30 minutes. The membrane is washed twice with 0.1M Tris-HCl (pH 7.5), 150 mM sodium chloride (buffer 1).

For the satuation of the DNA binding points, incubation is carried out for 30 minutes as above with 3 mg./ml. freshly denatured herring sperm DNA. Subsequently, washing is carried out twice with buffer 1 and the membrane immediately placed in the multi-filtration apparatus.

d) Hybridisation

Reaction batch: reaction volume 25 μl.
capturing probe (biotin-labelled) 5 ng.
detector probe (digoxigenin-labelled) 5 ng.
buffer 1 5×SSC=0.5M, NaCl, 50 mM sodium citrate
DNA to be detected 2 pg–1000 ng.

The reaction mixture is denatured for 5 minutes at 95° C. and subsequently incubated for 1 hour at 68° C. After cooling, the reaction mixture is incubated at ambient temperature for 15 minutes in the multi-filtration apparatus on the pre-treated membrane. Thereafter, the solution drawn into the membrane. It is briefly sucked off and then washed twice with, in each case, 50 μl. of buffer 1.

e) Detection pf the sandwich DNA complex e1) Blocking

The membrane is removed from the filtration apparatus and incubated for 40 minutes at ambient temperature, with shaking, in 3% fat-free dry milk in buffer 1.

e2) Immunological reaction

The blocked membrane is incubated for 30 minutes at ambient temperature, with shaking, in a 1:3000 dilution of anti-digoxigenin-antibody alkaline phosphatase conjugate in buffer 1.

e3) Washing

The membrane is washed three times with buffer 1 and once with 0.1M Tris-HCl (pH 9.5), 0.1M sodium chloride and 50 mM magnesium chloride.

e4) Colour reaction

The membrane is incubated in a fresh solution, flushed with nitrogen, of 0.33 mg./ml. nitro-tetrazole blue and 0.167 mg./ml. 5-bromo-4-chloro-3-indolyl phosphate with the exclusion of air and in the dark at ambient temperature, best sealed in a foil covering.

f) Results

With this process, 10 to 100 pg. of oligonucleotide DNA to be detected in 25 μl. reaction solution can be detected, which corresponds to a concentration of 4 ng./ml. The test period is about 6 hours. The evaluation of a measurement of the colour forming reaction is given in FIG. 6 of the accompanying drawings.

The addition of up to 5000 ng./ml. (=5 μg./ml.) of foreign DNA (herring sperm) does not result in a reduction of the signal.

Control Reactions

If sandwich hybridization batches are filtered on to a membrane, which had been coated with thermo-RSA, analogously to the above description, a background of 80 mE is measured. A dependence of the amount of sample DNA is not observed.

Control reactions in which either biotin capturing probe DNA or digoxigenin detection probe DNA are missing also show background values of 80 mE.

We claim:

1. A process for the detection of a target nucleic acid in a solution by hybridization with a labelled, single stranded nucleic acid probe present in the same solution, comprising:

(a) incubating the solution with a labelled single stranded nucleic acid probe, wherein said probe has at least one digoxigenin or digoxin steroid hapten molecule covalently bound thereto, via a bridge of at least four atoms in length, wherein said bridge is bound to a site on said probe which does not participate in hydrogen bridge formation with any target nucleic acid in said solution, wherein said site is selected from the group consisting of: position C5 of uracil, position C8 of adenine, position C8 of guanine, and position 2′ of ribose; incubating said solution with a nucleic acid capturing probe, wherein said capturing probe is bound to a solid matrix before, during, or after incubation with said solution, said nucleic acid capturing probe being complementary to said target nucleic acid at a region different from the region of said target nucleic acid to which said probe is complementary, wherein said capturing probe is bound to said solid matrix (1) adsorptively, (2) coordinately, (3) covalently, (4) via a binding system which comprises biotin and avidin or (5) via a binding system which comprises biotin and streptavidin so as to form a solid phase bound complex of (i) matrix bound capture probe, (ii) target nucleic acid present in said solution, and (iii) said labelled nucleic acid probe;

(b) separating solid phase bound complex from said solution, (c) contacting solid phase bound complex with a labelled antibody which specifically binds to said digoxigenin or digoxin steroid hapten molecule, and (d) determining target nucleic acid by determining any binding of said labelled antibody to said solid phase bound complex.

2. The process of claim 1, wherein said bridge consists of from 11 to 16 atoms.

3. The process of claim 1, wherein said bridge comprises at least one hydrophilic group.

4. The process of claim 1, wherein said bridge is linear.

5. The process of claim 1, wherein said bridge comprises a branched chain.

6. The process of claim 1, wherein said bridge is bound to C5 of uracil, C8 of adenine or C8 of guanine.

7. The process of claim 1, wherein said bridge is bound to 2′ position of ribose.

8. The process of claim 1, wherein said digoxigenin or digoxin steroid hapten is bound to said bridge via an ether bond, an amide bond, or an ester bond.

9. The process of claim 1, wherein said capture probe is bound to said solid matrix via a biotin-avidin binding system.

10. The process of claim 1, wherein said capture probe is bound to said solid matrix via a biotin-streptavidin binding system.

11. The process of claim 9, wherein one of said biotin and avidin is directly bound to the 5'-end or the 3'end of said capturing probe.

12. The process of claim 10, wherein one of said biotin and streptavidin is directly bound to 5'-and or the 3'end of said capturing probe.

13. The process of claim 1 wherein said solid matrix is selected from the group consisting of a nitrocellulose filter, a nylon filter, a plastic, a plexiglass, a plexiglass coated with nitrocellulose, a plexiglass coated with nylon, a plastic coated with nitrocellulose, a plastic coated with nylon, and a wall of a reaction vessel.

14. The process of claim 1, wherein the digoxin or digoxigenin has been incorporated into the nucleic acid probe enzymatically with an RNA polymerase, a DNA polymerase, an exonuclease or a reverse transcriptases and a digoxin or digoxigenin modified deoxy- or ribonucleoside triphosphase substrate.

15. The process of claim 1, wherein the digoxin or digoxigenin has been incorporated into the nucleic acid probe photochemically via photohapten.

16. The process of claim 1, wherein digoxin or digoxigenin has been incorporated into the nucleic acid probe chemically via oligo-desoxyribonucleotide synthesis, by the incorporation of protected nucleoside phosphoamidites modified with substitutable amino functions and, after removal of protective groups thereon, by reaction of the modified oligodesoxyribonucleotide with a member selected from the group consisting of activated ester, an activated amide or an activated ether of digoxin or digoxigenin.

17. The process of claim 1 further comprising detecting the complex via a labelled antibody directed against digoxin or digoxigenin wherein the antibody is labelled via an enzyme label, a radioactive label, a fluorescent label, a luminiscent or a bioluminescent label.

18. The process of claim 17 wherein said enzyme is alkaline phosphatase, a peroxidase or beta-galactosidase.

19. The process of claim 18 further comprising determining activity of said enzyme via redox system.

20. The process of claim 19 further comprising determining the activity of the said enzyme via a color forming system.

21. The process of claim 19 wherein said enzyme is alkaline phosphatase, further comprising determining the alkaline phosphate via a 5-bromo-4-chloro-3-indolyl phosphate/nitro blue tetrazolium redox system.

22. The process of claim 1, wherein at least one of said capture probe and said labelled nucleic acid probe comprises a poly d(C) or a poly d(G) sequence.

* * * * *

UNITED STATES PATENT AND TRADEMARK OFFICE
CERTIFICATE OF CORRECTION

PATENT NO. : 5,354,657
DATED : October 11, 1994
INVENTOR(S) : Hans J. Koltke, et al.

It is certified that error appears in the above-indentified patent and that said Letters Patent is hereby corrected as shown below:

On title page, item [54] and col. 1, in title, change "SOLID" to ---SOLUTION---

On title page, add the following: item [73]

-- Assignee: Boehringer Mannheim GmbH, Mannheim-Waldorf, Germany.

Attorney Agent or Firm: Felfe & Lynch --.

Signed and Sealed this

Sixteenth Day of May, 1995

*Attest:*

BRUCE LEHMAN

*Attesting Officer*     Commissioner of Patents and Trademarks